United States Patent [19]
Ling et al.

[11] Patent Number: 6,077,960
[45] Date of Patent: Jun. 20, 2000

[54] URETEDIONE DERIVATIVE, CURABLE RESIN COMPOSITION COMPRISING THE SAME, AND PROCESS FOR PRODUCING THE SAME

[75] Inventors: Hao-Jan Ling, I-Lan Hsien; Kan-Nan Chen, Taipei; Jian-Zei Lai, Chia-Yi; Yun-Shan Lin, Taipei Hsien, all of Taiwan

[73] Assignee: Chinese Petroleum Corporation, China

[21] Appl. No.: 09/440,245

[22] Filed: Nov. 15, 1999

[51] Int. Cl.[7] .......................... C07D 403/14; C08G 18/80
[52] U.S. Cl. .............................................. 548/951; 528/45
[58] Field of Search ................................ 548/951; 528/45

[56] References Cited

U.S. PATENT DOCUMENTS 5,719,240   2/1998   Gras et al. ........................... 528/45 X

FOREIGN PATENT DOCUMENTS 1488631   10/1977   United Kingdom .

*Primary Examiner*—Fiona T. Powers
*Attorney, Agent, or Firm*—Ostrolenk, Faber, Gerb & Soffen, LLP

[57] ABSTRACT

A novel uretedione derivative used as a curing agent for aqueous-based polyurethane and a process for producing the same are disclosed. The uretedione derivative contains uretedione and aziridine functional groups which are active toward the amino and the carboxy groups of hydrolyzed polyurethane in an aqueous phase.

14 Claims, No Drawings

URETEDIONE DERIVATIVE, CURABLE RESIN COMPOSITION COMPRISING THE SAME, AND PROCESS FOR PRODUCING THE SAME

BACKGROUND OF THE INVENTION

1. Field of the Invention

The present invention relates to a uretedione derivative, more particularly to a uretedione derivative for aqueous-based polyurethane.

2. Description of the Related Art

Polyurethanes are a type of polymers that can have widely differing properties. Such versatility and multitude properties permit some of the polyurethanes to exhibit an elasticity and a flexibility similar to those of rubbers, and others to exhibit a mechanical strength and a hardness similar to those of plastics. As such, polyurethanes are wildly used in the manufacture of products, such as shoesoles, synthetic leathers, adhesives, sealants, printing inks, foams, films, coatings, and fiber modifiers.

Applications of solvent-based polyurethanes and technologies for the process of producing the same are well developed. However, due to problems with respect to the environment, economy, sanitation, and safety, the solvent-based polyurethane tends to be gradually replaced by aqueous-based polyurethane which is an environmental friendly product that dispenses with the use of the solvent.

While there has been a great demand for aqueous-based polyurethane, the physical and mechanical properties of the same are still insufficient in comparison with those of the solvent-based polyurethane. Difficulties have been encountered for current technologies for producing aqueous-based polyurethane in enhancing the molecular weight and the cross-linking density of the polyurethane. Such properties are often improved by post-curing reaction which unfortunately results in limiting the applications of the aqueous-based polyurethane.

There are several types of self-emulsifiable aqueous-based polyurethane available in the market. These aqueous-based polyurethanes can be classified into non-ionic, cationic, and anionic aqueous-based polyurethanes depending on the nature of the hydrophilic group of the polyurethane. For instance, when dissolved in water, the carboxy groups of the anionic aqueous-based polyurethane provide surface charges to the surrounding of the polyurethane molecules (particles), thereby causing repulsion between the polyurethane molecules (particles) and resulting in uniform distribution of the polyurethane molecules in the water phase. Such behavior permits the aqueous-based polyurethane to form into a polyurethane emulsion upon mixing with water, and is similar to a surfactant which acts as an emulsifier and which is formed into a plurality of micro-cells in a water phase. Because of the hydrophilic property of the carboxy group, the polyurethane becomes self-emulsifiable or water-reducible in the water phase. Such aqueous-based polyurethanes have a common disadvantage similar to that of a polymeric surfactant in that, after drying into a film, such film exhibits a high water absorptivity.

As described in the publications, the improvements on aqueous-based polyurethane are normally performed by post-curing reaction to enhance the molecular weight and the cross-linking density of the polyurethane so as to broaden the applications of the same. Conventionally, such post-curing reaction is carried out by mixing "two components" together, i.e., adding a liquid containing the post-curing agent into another liquid containing the aqueous-based polyurethane before the application. However, such mixing of "two components" may result in instability to the quality of the polyurethane products due to the variations of the ratio of the "two components" and the degree of the uniformity of the agitation. The occurrence of such instability is particularly severe in a batch process, and can significantly restrict the applications of the aqueous-based polyurethane.

In the case of the process for producing anionic (carboxy group) polyurethane emulsion, the addition of water into an isocyanate-terminated urethane prepolymer is an essential step to form the polyurethane emulsion. The formation of the anionic carboxy group polyurethane emulsion is better described from the following scheme:

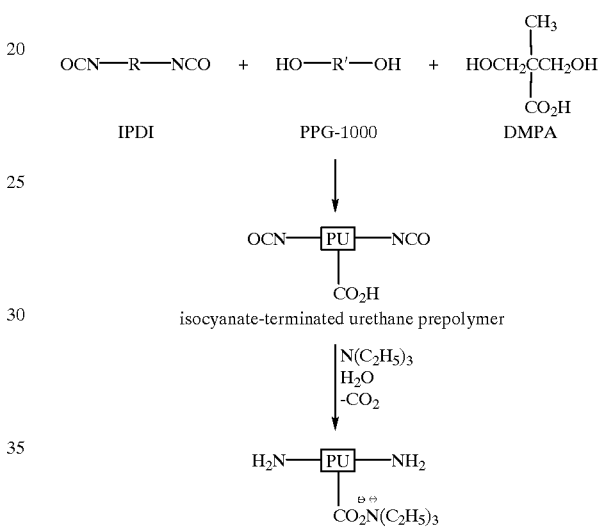

As described in the above reaction scheme, isocyanate-terminated urethane prepolymer is prepared by reacting isophorone diisocyanate with polypropylene glycol in the presence of dimethylpropionic acid. The terminal isocyanate groups of the thus formed urethane prepolymer are hydrolyzed to amino groups by water. The amino groups of the urethane prepolymer may result in a self-chain extending reaction by reacting with the isocyanate groups of the urethane prepolymer to form urea bonding, or may be present in the water phase without further reaction. While the presence of the amino groups and the carboxy groups of the aqueous-based polyurethane can stabilize the polyurethane emulsion, they also result in high water absorptivity which significantly affects the subsequent processing of the polyurethane emulsion, such as dyeing.

SUMMARY OF THE INVENTION

Therefore, it is an object of the present invention to provide a curing agent containing a uretedione derivative which is capable of overcoming the problems described above.

According to one aspect of the present invention, there is provided a uretedione derivative having the following formula (I):

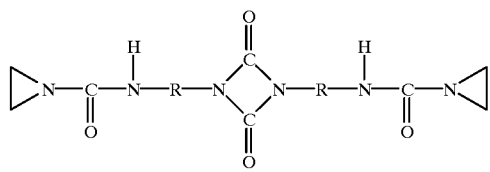

(I)

wherein R represents a unsubstituted or substituted $C_1$–$C_{20}$ hydrocarbyl group.

According to another aspect of the present invention, there is provided a curable resin composition comprising the uretedione derivative of formula (I) and a resin which is reactive toward the uretedione derivative.

According to yet another aspect of the present invention, there is provided a process for producing the uretedione derivative of formula (I), comprising the step of reacting a uretedione with an aziridine to form the uretedione derivative.

DETAILED DESCRIPTION OF THE INVENTION

The above described instability and high water absorptivity for the aqueous-based polyurethane can be eliminated by introducing a curing agent discovered in the present invention into an isocyanate-terminated urethane prepolymer.

The curing agent of this invention contains a uretedione derivative which is prepared by addition reaction of a uretedione with an aziridine to form a compound containing uretedione and aziridine functional groups and having the following formula:

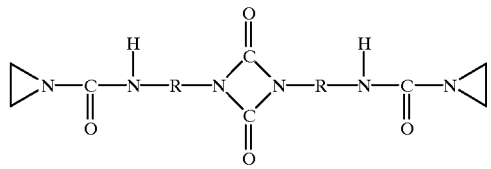

wherein R represents a unsubstituted or substituted $C_1$–$C_{20}$ hydrocarbyl group. The above reaction and the reaction for preparing the uretedione can be illustrated in the following scheme:

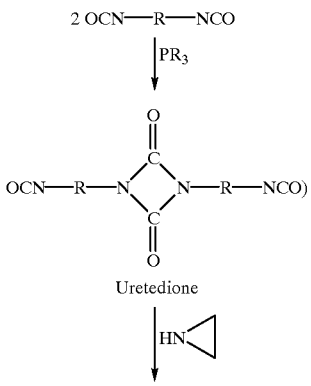

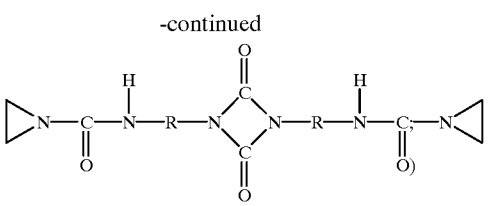

Uretediones can be prepared in the presence of a specific catalyst, such as triethylphosphines, through dimerization of aliphatic diisocyanates, such as isophorone diisocyanate (IPDI), hexamethylene diisocyanate (HDI), and hydrogenated methylene diphenyl 4,4'-diisocyanate ($H_{12}$MDI).

With the above described curing agent of this invention, the isocyanate-terminated urethane prepolymer can be transformed into a self-curable urethane prepolymer which will form into a "single component" self-curable polyurethane emulsion when mixed with water. The term "single component" used herein is simply to distinguish from the above described "two components", and that it can be understood that the polyurethane emulsion according to this invention is self-curable, thereby dispensing from the use of an additional liquid containing post-curing agent. The role of the curing agent of this invention can be better understood by the following description.

Before forming into a polyurethane emulsion, the isocyanate-terminated urethane prepolymer is simply mixed with the uretedione derivative of formula (I) without reacting with the latter. When further mixed with water to form the polyurethane emulsion, the terminal isocyanate groups of the isocyanate-terminated urethane prepolymer are first hydrolyzed into amino groups which then immediately undergo an addition reaction with the uretedione groups of the uretedione derivative contained in the above described mixture to form urea bonding, thereby resulting in a cross-linking reaction. Such cross-linking reaction is carried out through the ring-opening of the uretedione, and is illustrated by the following scheme:

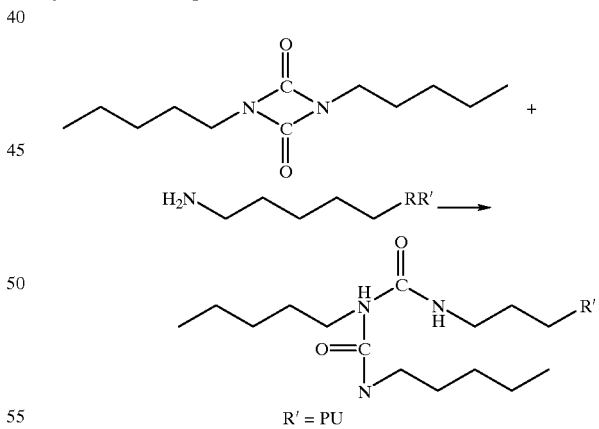

R' = PU

After the ring opening of the uretedione, the uretedione derivative originally contained in the mixture becomes part of the cross-liked polyurethane in the polyurethane emulsion, thereby introducing the aziridine groups therein. The polyurethane emulsion according to this invention normally has a pH value greater than 8. At such condition, the introduced aziridine groups are retained in a stable condition in the polyurethane emulsion. When the polyurethane emulsion is subjected to a drying operation, the pH value of the emulsion will decrease. When the pH value decreases to less than 6, the carboxy group of the cross-linked polyurethane will start reacting with the introduced aziridine groups, thereby resulting in another cross-linking reaction through the ring-opening of the aziridine. Such cross-linking reaction can be illustrated by the following scheme:

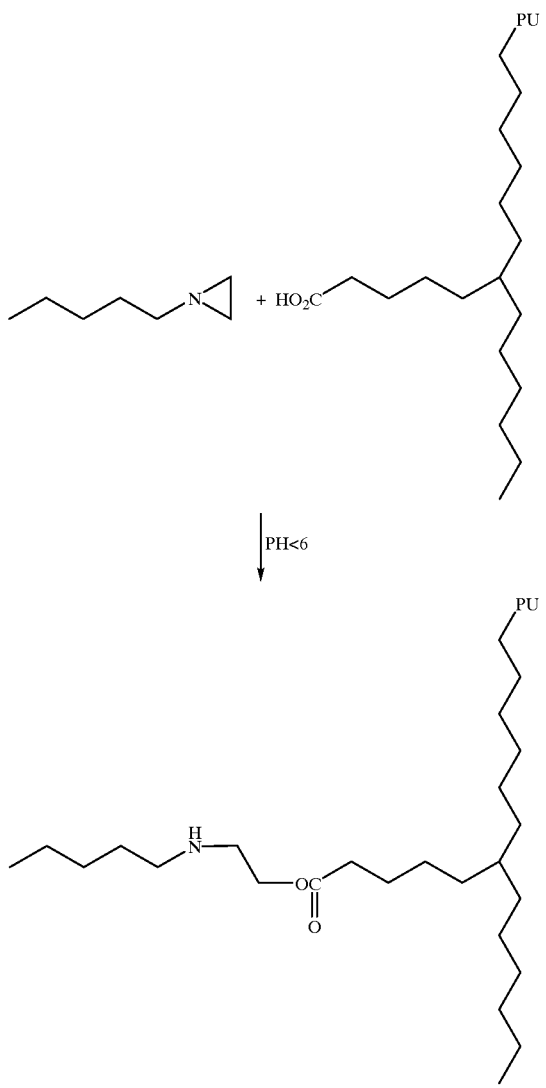

The invention will now be specifically described by the following examples which are not meant to limit the scope of this invention.

Example 1

A round-bottom flask was charged with 20 g of isophorone diisocyante (IPDI) and 0.5% by weight of triethyl phosphine, based on the total weight of the above two compounds. Dimerization of the isophorone diisocyante for forming the uretedione was carried out in a water bath at a temperature ranging from 85 to 90° C. The reaction was terminated when the isocyanate number reached a stoichiometric number which was half of the initial isocyanate number. Five grams of aziridine was added dropwise into the flask to react with the above formed uretedione to form the curing agent of this invention. The reaction was carried out at a temperature of 50° C. for about 2 hours. The reaction was completed when the isocyanate number dropped to about zero (i.e., the absorption peak based on the NCO group was not observed at 2261 $cm^{-1}$ in the infrared spectrum measurement). The thus formed curing agent exhibits two new absorption peaks which are observed at 1540 and 1668 $cm^{-1}$ in the infrared spectrum measurement and which represent the uretedione and the aziridine functional groups of the curing agent, respectively.

Example 2

Isophorone diisocyanate (IPDI), polypropylene glycol (PPG-1000), and dimethylolpropanic acid (DMPA) were used as the starting material for the preparation of the isocyanate-terminated urethane prepolymer. The ratio of IPDI:PPG-1000:DMPA was 4:2:1. Reaction was carried out at a temperature ranging from 95 to 100° C. for about 4 hours. The reaction was completed when the isocyanate number reached 3.5%, based on the initial number of the isocyanate number contained in the reactants. The thus formed NCO-terminated urethane prepolymer was then cooled to room temperature. 100 g of the above prepolymer was mixed with 3.7 g of the curing agent obtained from Example 1. The above formed mixture was neutralized with triethyl amine, and was diluted with acetone to obtain a workable viscosity (e.g. 1000 cps). The diluted mixture was then added with water to form the aqueous-based polyurethane emulsion. The polyurethane emulsion was subjected to drying to form a polyurethane film. The measured tensile strengths of the above formed polyurethane film were 2.2 $kg/cm^2$ with an elongation of 100%, 3.8 $kg/cm^2$ with an elongation of 200%, and 7.9 $kg/cm^2$ with an elongation of 500%. With the same corresponding elongations described above, the measured tensile strengths of an aqueous-based polyurethane film which had not been cross-linked were 0.5, 1.0, and 1.9 $kg/cm^2$, respectively. The polyurethane film formed in this example also exhibits a gel content of 94.7% and an ethanol-swollen of 377.5%. The aqueous-based polyurethane film which had not been cross-linked is soluble in solvent, such as tetrahydrofuran (THF) and ethanol.

Example 3

A curing agent of this invention was prepared according to the same procedure as that of Example 1 except that the IPDI was replaced by $H_{12}MDI$. A polyurethane film containing the above formed curing agent was formed by performing the same procedure as that of Example 2. The measured tensile strengths of the thus formed polyurethane film were 4.3 $kg/cm^2$ with an elongation of 100% and 7.0 $kg/cm^2$ with an elongation of 200%. The polyurethane film formed in this example also exhibits a gel content of 97.5% and an ethanol-swollen of 220%.

The invention shall not be limited by the embodiments described above, which are exemplary and which can be modified in various ways within the scope of protection defined by the appended patent claims.

We claim:

1. A uretedione derivative having the following formula (I):

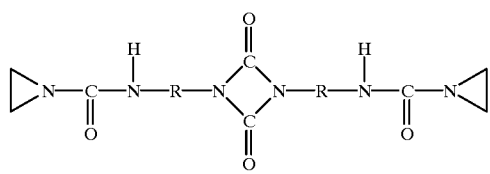

wherein R represents a unsubstituted or substituted $C_1$–$C_{20}$ hydrocarbyl group.

2. The uretedione derivative of claim 1, wherein said uretedione derivative is prepared by reacting a uretedione with an aziridine.

3. The uretedione derivative of claim 2, wherein said uretedione is prepared by dimerizing a diisocynate.

4. The uretedione derivative of claim 3, wherein said diisocynate is selected from the group consisting of isophorone diisocyanate, hexamethylene diisocyanate, and hydrogenated methylene diphenyl 4,4'-diisocyanate.

5. A curable resin composition, comprising a uretedione derivative of formula (I) of claim 1 and a resin which is reactive toward said uretedione derivative.

6. The curable resin composition of claim 5, wherein said resin comprises amino and carboxy groups.

7. The curable resin composition of claim 5, wherein said uretedione derivative is prepared by reacting a uretedione with an aziridine.

8. The curable resin composition of claim 7, wherein said resin is an isocyanate-terminated urethane prepolymer having terminal isocyanate groups.

9. The curable resin composition of claim 8, further comprising water which reacts with said isocyanate groups of said resin to form amino groups.

10. The curable resin composition of claim 9, wherein said uretedione group of said uretedione derivative reacts with said amino groups of said resin at a pH value >8 to form urea bonding.

11. The curable resin composition of claim 10, wherein said urethane prepolymer comprises a carboxy group which reacts with said aziridine group of said uretedione derivative at a pH value <6.

12. A process for producing a uretedione derivative of formula (I) of claim 1, comprising the step of reacting a uretedione with an aziridine to form said uretedione derivative.

13. The method of claim 12, wherein said uretedione is prepared by dimerizing a diisocynate.

14. The method of claim 13, wherein said diisocynate is selected from the group consisting of isophorone diisocyanate, hexamethylene diisocyanate, and hydrogenated methylene diphenyl 4,4'-diisocyanate.

* * * * *